(12) United States Patent
Villa et al.

(10) Patent No.: US 12,337,052 B2
(45) Date of Patent: Jun. 24, 2025

(54) HAIR TREATMENT METHOD THAT INCREASES THE BOND DENSITY OF DAMAGED HAIR

(71) Applicant: BEAUTY & BUSINESS S.p.A., Milan (IT)

(72) Inventors: Giovanni Villa, Cornate d'Adda (IT); Emanuela Facchetti, Romano di Lombardia (IT)

(73) Assignee: BEAUTY & BUSINESS S.p.A., Milan (IT)

( * ) Notice: Subject to any disclaimer, the term of this patent is extended or adjusted under 35 U.S.C. 154(b) by 0 days.

(21) Appl. No.: 18/354,677

(22) Filed: Jul. 19, 2023

(65) Prior Publication Data
US 2024/0033199 A1    Feb. 1, 2024

(30) Foreign Application Priority Data
Jul. 20, 2022   (IT) .................. 102022000015243

(51) Int. Cl.
*A61Q 5/10*   (2006.01)
*A61K 8/44*   (2006.01)
*A61Q 5/00*   (2006.01)

(52) U.S. Cl.
CPC .............. *A61K 8/442* (2013.01); *A61Q 5/002* (2013.01); *A61Q 5/10* (2013.01); *A61K 2800/4322* (2013.01)

(58) Field of Classification Search
CPC .. A61K 8/442; A61K 2800/4322; A61K 8/44; A61K 2800/432; A61Q 5/002; A61Q 5/10; A61Q 5/065; A61Q 5/08; A61Q 5/12

USPC .............................................. 8/405
See application file for complete search history.

(56) References Cited

U.S. PATENT DOCUMENTS

2007/0299137 A1   12/2007   Comini et al.

FOREIGN PATENT DOCUMENTS

| DE | 102006011317 A1 | 2/2007 | |
|----|-----------------|--------|---|
| DE | 102005056157 A1 * | 5/2007 | ............... A61Q 5/10 |
| DE | 102008059443 A1 * | 6/2010 | ............... A61K 8/06 |
| WO | 2003063851 A1 | 8/2003 | |

OTHER PUBLICATIONS

DR Dennis Gross Skincare: "Anti-aging scalp serum", Oct. 1, 2013.
Rigano L. et al., "Azeloyl-Glycine: a new active in skin disequilibrium", Journal of Applied Cosmetology, International Ediemme, Rome, IT, vol. 21, Oct. 1, 2003, pp. 177-188.
Search Report and Written Opinion of Priority Application IT 202200015243 issued Feb. 21, 2023.

* cited by examiner

*Primary Examiner* — Eisa B Elhilo
(74) *Attorney, Agent, or Firm* — Silvia Salvadori, P.C.; Silvia Salvadori

(57) ABSTRACT

Keratinic fiber treatment methods that increase the bond density of damaged hair are disclosed, the methods include the application to the hair of potassium azeloyl diglycinate in weight percentages ranging between 0.1 and 6%, preferably between 0.5 and 3%.

8 Claims, 2 Drawing Sheets

HAIR TREATMENT METHOD THAT INCREASES THE BOND DENSITY OF DAMAGED HAIR

This application claims priority to and the benefit of Italian Patent Application No. 102022000015243, filed Jul. 20, 2022, the contents of which is incorporated herein by reference in its entirety.

The invention relates to a keratinic fiber treatment method that increases the bond density of damaged hair.

PRIOR ART

Cosmetic hair treatments, such as bleaching, permanent dyeing and permanent styling, often damage the hair structure. Following said treatments, especially if repeated, the hair tends to become fragile, dull and unmanageable. There is consequently a real need to preserve and improve the quality of the fibre, optimising the density of the bond between the proteins to guarantee the strength and cosmetic properties of the hair.

The hair structure consists of alpha-keratin chains. The strength of the hair is based on said polypeptide keratin helices oriented parallel to the longitudinal axis of the hair fibre. The helical structure is stabilised by hydrogen bonds, ionic, hydrophobic and coulombian interactions, and covalent bonds such as disulphide bridges.

The greater the density of all of said bonds, the stronger the hair.

Hair is dyed not only to conceal grey areas, but also to personalise its colour on the basis of fashions. To change the hair colour radically and obtain the desired result, it is often necessary to perform a lightening treatment using bleaching products in powder or cream form based on persulphates and silicates which lighten the hair by up to nine levels, or permanent oxidative dyes.

Oxidative dyes lighten the natural colour of the keratin fibre by up to four levels, enabling the hair colour to be changed radically and white hair to be covered. They are currently stable for four to six weeks under normal conditions, and are therefore called "permanent" dyes.

The oxidative system is based on the reaction of "primary intermediates" with couplers; both types of molecules are colourless. In the presence of air or oxidants, primary dyes, which are primary aromatic amines with a hydroxyl or additional amino group, substituted or not substituted, in the para or ortho position, react with couplers such as resorcinol, m-aminophenol, m-phenylenediamine, 1-naphthol and pyridine.

As the dye molecules thus formed in the cuticle are larger than the starting primary intermediates and the highly diffusible couplers, they remain trapped inside the hair, and there is therefore no significant fading due to successive washes or the action of external agents. Oxidative dyes also require the presence of an alkalising agent. Ammonia is the alkalising agent most commonly used.

Hydrogen peroxide is the oxidising agent mainly used for both bleaching and permanent dyeing of the hair. The formulations on the market are stabilised to an acid pH (pH 2-3), and to obtain the full oxidising effect they need to be "activated" by mixing them with an alkaline agent (oxidative dye or bleaching powder). Under said conditions a mixture with a pH ranging between 9 and 11 is generated which opens the cuticles, allows the bleaching/dyeing agents to penetrate the cortex, and triggers the radical oxidation reaction needed to destroy the melanin granules.

The colour "level" or "height of tone" indicates the depth of the colour, i.e., how light or dark the hair is. The ICC (International Colour Chart) system uses numbers to define the depth of colour. Said values range from 1 to 11, wherein 1 denotes the darkest shade (black) and 11 the lightest shade (platinum blonde).

The usual level numbers and names are as shown in Table A.

TABLE A

| Level | Level name |
| --- | --- |
| 1 | Black |
| 2 | Very dark brown |
| 3 | Dark brown |
| 4 | Medium brown |
| 5 | Light brown |
| 6 | Dark blonde |
| 7 | Medium blonde |
| 8 | Light blonde |
| 9 | Very light blonde |
| 10 | Lightest blonde |
| 11 | Platinum blonde |

"Lightening" is therefore defined as the change from a darker to a lighter level by means of a chemical treatment that gives rise to oxidative destruction of the melanin granules in the hair cortex.

Many customers also wish to change their hair shape permanently, from straight to curly or vice versa. Very alkaline compositions are used to achieve said result, sometimes combined with high-temperature heat sources (150-230° C.). The products used can be agents based on reducing thiols (e.g. ammonium thioglycolate or thioglycolic acid), to curl or straighten the hair, or lotions containing strong bases (e.g. sodium hydroxide or guanidine hydroxide), only used in this case to straighten extremely curly hair. Permanent bleaching/dyeing or permanent styling treatments are aggressive to the hair fibre.

High pH levels and/or oxidative reactions have a strong impact on the chemical structure of the hair, and also reduce the free and bonded lipid content of the hair cuticle, thus converting the hair surface from a hydrophobic entity with little surface charge to a more hydrophilic, more polar and more negatively charged surface.

Damaged hair is thus drier, more difficult to brush, breaks more easily and is duller and less glossy.

Methods and compositions for protecting the bonds in the hair fibre during the more aggressive cosmetic treatments have been described. See, for example, patent applications WO2017091794, WO2018191362 and WO2019198114.

In the last ten years, various products designed to protect the hair fibre during the more aggressive chemical treatments have been launched on the market. Said products are kits consisting of two compositions, one of which is designed to be mixed with a cosmetic bleaching/dyeing/permanent styling treatment to protect the hair, while the other is applied at the end of the treatment to seal the cuticles.

Many of said products are based on polycarboxylic acids or derivatives thereof, in particular malic or maleic acid.

Nearly all the products designed to be mixed with the cosmetic treatment have a pH of 3-4 which alters the pH of the bleaching/dyeing/permanent styling treatment (which is between 9 and 11), thus prejudicing the result, as stated in WO2018191362. It should be noted that adding a composition to the bleach, dye or permanent styling product, even at a compatible pH, still involves dilution of the active ingredients and possible interaction with them, which may prejudice or alter the result. Moreover, the use of a two-component kit is expensive for the customer.

There are some permanent oxidative dyes on the market which claim "pre-bonding" ingredients designed to protect the hair against possible damage caused by the dye.

There are also conditioners or masks containing direct dyes (semipermanent colouring compositions wherein the dyes bond to the hair surface via ionic bonds) claiming "bonding" ingredients designed to repair hair damaged by bleaching. However, the efficacy of said one-step products is unsatisfactory.

There is consequently a need for a single treatment that not only protects the hair against chemical damage, but also restores, in a single step, with a single application along the hair fibre, the strength and cosmetic properties of hair damaged by prior treatments, without interfering in any way with the performance of the dyeing/bleaching/permanent styling treatment.

The purpose of the invention is to provide a composition able to restore the natural bond density of the hair, leaving it conditioned and glossy.

DESCRIPTION OF THE INVENTION

Figure 1:
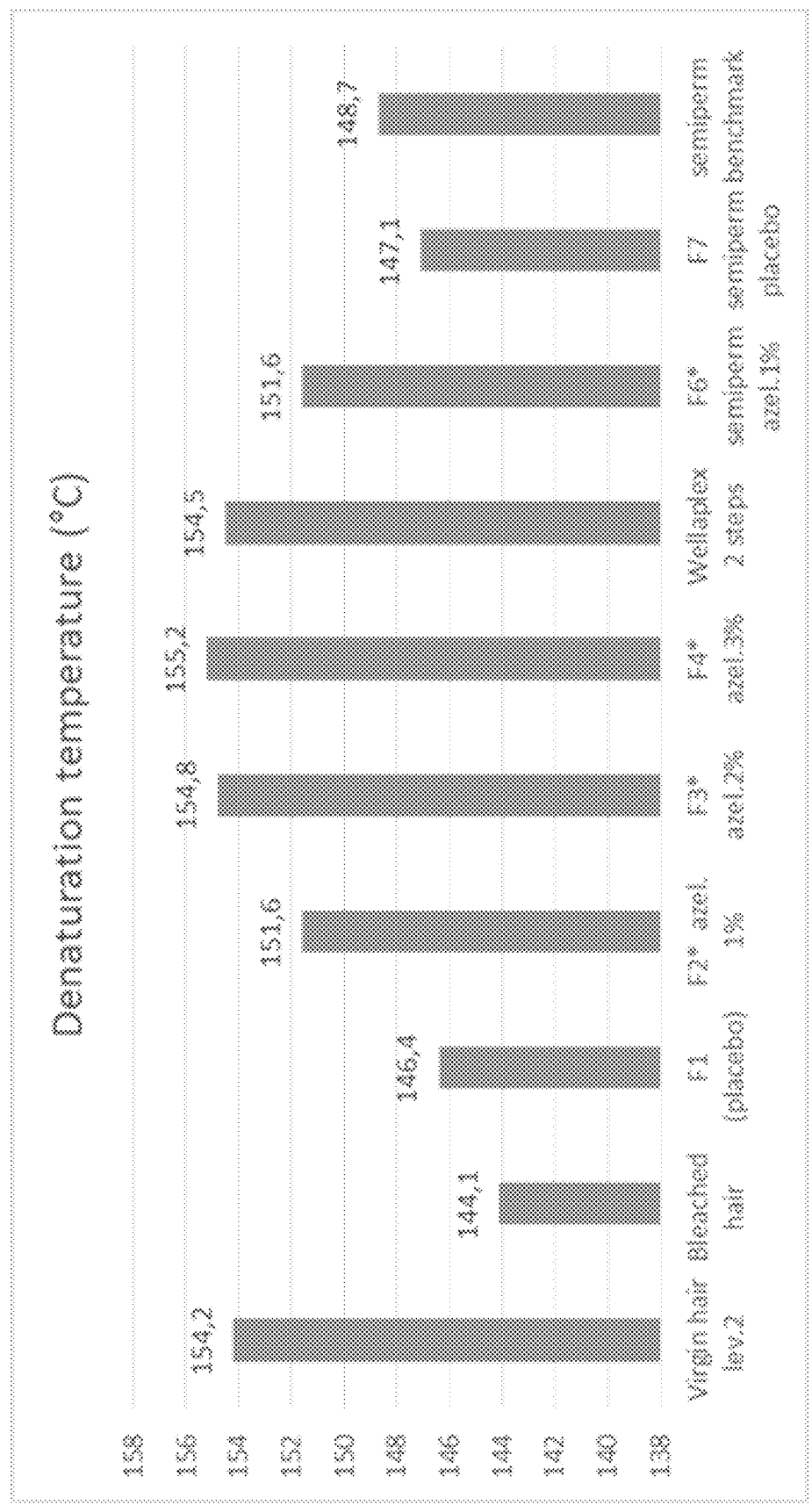
FIG. 1 shows the mean denaturation temperatures TD measured from the various samples.

It has been found that compositions containing 0.1 to 6% by weight, preferably 0.5 to 3% by weight, of azeloglycine (potassium azeloyl diglycinate) increase the bond density of damaged hair, restoring the natural hair values, or even better values.

Said compositions can have a pH ranging from 3 to 11 and can be applied also to keratinic fibers other than human hair, for example to pet hair.

The object of the present invention is therefore a method for increasing the bond density of damaged hair, which comprises direct application to the hair of compositions containing 0.1 to 6% by weight, preferably 0.5 to 3% by weight, of azeloglycine (potassium azeloyl diglycinate).

The compositions usable in the method according to the invention can optionally contain direct dyes or oxidative dyes; the pH of the compositions containing only direct dyes falls into the range of 3 to 9, preferably 3 to 6, while the pH of the compositions also containing oxidative dyes falls into the range of 8 to 11.

Azeloglycine is known in the cosmetic industry as a sebum-regulating, brightening and lightening ingredient for the skin. Azeloglycine is an active ingredient useful in controlling skin imbalances (Rigano L. et al.: "Azeloylglycine: a new active in skin disequilibrium" Journal of Applied Cosmetology, International Ediemme, Rome, It, Vol 21, 1 Oct. 2023, pp. 177-188); said ingredient, or derivatives thereof, can therefore be used in treatments designed to address scalp problems such as dandruff and alopecia (US2007299137). Azeloglycine and the salts thereof are therefore known for their use as anti-hair loss and hair reinforcing agents, but involving regular, repeated applications to the scalp (e.g. Dr Dennis Gross Skincare scalp serum) to promote the birth of stronger hair by means of skin care. Azeloglycine has never been used for restructuring treatment of hair fibres damaged by external agents or aggressive cosmetic treatments. The efficacy of azeloglycine or the salts thereof as agents able to create new bonds in the hair fibre is therefore surprising, and unforeseeable. The composition according to the invention can take the form of an O/W (oil-in-water) or W/O (water-in-oil) emulsion, liquid, two-phase liquid, gel, transparent gel, oil, aerosol or mousse.

It can be a mask/conditioner/shampoo optionally containing direct dyes designed to be applied directly to the hair (not to the skin) and left to act for 5 to 30 minutes, preferably 10 to 20 minutes, and then rinsed; or can be a permanent oxidative dye designed to be mixed with a hydrogen peroxide-based composition at the ratio of 1:1 to 1:2 and left to act on the hair for 10 to 60 minutes, preferably 25-40 minutes, and then rinsed.

The oxidative dye is preferably selected from 1-Acetoxy-2-Methylnaphthalene, 5-Amino-4-Chloro-o-Cresol, 4-Amino-m-Cresol, 6-Amino-m-Cresol, 3-Amino-2,4-Dichlorophenol, 6-Amino-2,4-Dichloro-m-Cresol, 3-Amino-2,4-Dichlorophenol, 5-Amino-2,6-Dimethoxy-3-Hydroxypyridine, 5-Amino-2,6-Dimethoxy-3-Hydroxypyridine, 3-Amino-2,6-Dimethylphenol, 2-Amino-5-Ethylphenol, 5-Amino-4-Fluoro-2-Methylphenol Sulphate, 2-Amino-4-Hydroxyethylaminoanisole, 2-Amino-4-Hydroxyethylaminoanisole, 2-Amino-3-Hydroxypyridine, 4-Amino-2-Hydroxytoluene, 2-Aminomethyl-p-Aminophenol, 4-Amino-2-Nitrodiphenylamine-2'-Carboxylic Acid, m-Aminophenol, o-Aminophenol, p-Aminophenol, 1,3-Bis-(2,4-Diaminophenoxy)propane, 4,6-Bis(2-Hydroxyethoxy)-m-Phenylenediamine, 2,6-Bis(2-Hydroxyethoxy)-3,5-Pyridinediamine, N,N-Bis(2-Hydroxyethyl)-p-Phenylenediamine, 4-Chloro-2-Aminophenol, 2-Chloro-p-Phenylenediamine, 4-Chlororesorcinol, N-Cyclopentyl-m-Aminophenol, 3,4-Diaminobenzoic Acid, 4,5-Diamino-1-(4-Chlorophenyl)Methyl)-1H-Pyrazole-Sulphate, 2,3-Diaminodihydropyrazolo Pyrazolone Dimethosulphonate, 2,4-Diaminodiphenylamine, 4,4'-Diaminodiphenylamine, 2,4-Diamino-5-Methylphenetole, 2,4-Diamino-5-Methylphenoxyethanol, 4,5-Diamino-1-Methylpyrazole, 2,4-Diaminophenol, 2,4-Diaminophenoxyethanol, 2,6-Diaminopyridine, 2,6-Diamino-3-((Pyridin-3-yl)Azo)Pyridine, N,N-Diethyl-m-Aminophenol, N,N-Diethyl-p-Phenylenediamine, N,N-Diethyltoluene-2,5-Diamine, 2,6-Dihydroxy-3,4-Dimethylpyridine, 2,6-Dihydroxyethylaminotoluene, Dihydroxyindole, 5,6-Dihydroxyindoline, 2,6-Dimethoxy-3,5-Pyridinediamine, m-Dimethylaminophenyl Urea, N,N-Dimethyl-p-Phenylenediamine, 2,6-Dimethyl-p-Phenylenediamine, N,N-Dimethyl 2,6-Pyridinediamine, 4-Ethoxy-m-Phenylenediamine, 3-Ethylamino-p-Cresol, 4-Fluoro-6-Methyl-m-Phenylenediamine, 1-Hexyl 4,5-Diamino Pyrazole Sulphate, Hydroquinone, Hydroxyanthraquinoneaminopropyl Methyl Morpholinium Methosulphate, Hydroxybenzomorpholine, Hydroxyethoxy Aminopyrazolopyridine, Hydroxyethylamino-methyl-p-Aminophenol, 1-Hydroxyethyl 4,5-Diamino Pyrazole, Hydroxyethyl-2,6-Dinitro-p-Anisidine, Hydroxyethyl-3,4-Methylenedioxyaniline, Hydroxyethyl-p-Phenylenediamine, 2-Hydroxyethyl Picramic Acid, 6-Hydroxyindole, Hydroxypropyl Bis(N-Hydroxyethyl-p-Phenylenediamine), Hydroxypropyl-p-Phenylenediamine, Hydroxypyridinone, Isatin, N-Isopropyl 4,5-Diamino Pyrazole, N-Methoxyethyl-p-Phenylenediamine, 6-Methoxy-2-methylamino-3-aminopyridine, 2-Methoxymethyl-p-Aminophenol, 2-Methoxymethyl-p-Phenylenediamine, 2-Methoxy-p-Phenylenediamine, 6-Methoxy-2,3-Pyridinediamine, 4-Methoxytoluene-2,5-Diamine, p-Methylaminophenol, 4-Methylbenzyl 4,5-Diamino Pyrazole, 2,2'-Methylenebis 4-Aminophenol, 3,4-Methylenedioxyaniline, 3,4-Methylenedioxyphenol, 2-Methyl-5-Hydroxyethyl-aminophenol, Methylimidazoliumpropyl p-Phenylenediamine, 2-Methyl-1-Naphthol, 2-Methylresorcinol, 1,5-Naphthalenediol, 1,7-Naphthalenediol, 2,3-Naphthalenediol, 2,7-Naphthalenediol, 1-Naphthol, 2-Naphthol, PEG-3 2,2'-Di-p-Phenylenediamine, p-Phenetidine, m-Phenylenediamine, Phenyl Methyl Pyrazolone, N-Phenyl-p-Phenylenediamine, Picramic Acid, Pyrocatechol, Pyrogallol, Resorcinol, Sodium Picramate, Tetraaminopyrimidine, Tetrahydro-6-Nitroquinoxaline, Tetrahydropyranyl, Resorcinol, Toluene-2,5-Diamine, Toluene-2,6-Diamine, Toluene-3,4-Diamine, 2,5,6-Triamino-4-Pyrimidinol, 1,2,4-Trihydroxybenzene. The oxidative dyes can take the form of salts.

The direct dye can be selected from Acid green 25, Acid red 92, Acid red 95, 2-Amino-6-Chloro-4-Nitrophenol, 4-Amino-2-Nitrodiphenylamine-2'-Carboxylic Acid, 2-Amino-3-Nitrophenol, 2-Amino-4-Nitrophenol, 2-Amino-5-Nitrophenol, 4-Amino-2-Nitrophenol, 4-Amino-3-Nitrophenol, Basic Blue 99, Basic Blue 124, Basic Brown 4, Basic Brown 16, Basic Brown 17, Basic Orange 31, Basic Red 1, Basic Red 51, Basic Red 76, Basic Red 118, Basic Violet 2, Basic Violet 14, Basic Violet 16, Basic Yellow 40, Basic Yellow 57, Basic Yellow 87, N,N'-Bis(2-Hydroxyethyl)-2-Nitro-p-Phenylenediamine, 2-Chloro-6-Ethylamino-4-Nitrophenol, 2-Chloro-5-Nitro-N-Hydroxyethyl p-Phenylenediamine, N,N'-Dimethyl-N-Hydroxyethyl-3-Nitro-p-Phenylenediamine, Direct Black 51, Disperse Blue 377, Disperse Violet 1, HC Blue No. 2, HC Blue No. 10, HC Blue No. 11, HC Blue No. 12, HC Blue No. 13, HC Blue No. 14, HC Blue No. 15, HC Blue No. 16, HC Blue No. 17, HC Blue No. 18, HC Orange No. 1, HC Orange No. 2, HC Red No. 3, HC Red No. 10, HC Red No. 11, HC Red No. 13, HC Violet No. 1, HC Violet No. 2, HC Yellow No. 2, HC Yellow No. 4, HC Yellow No. 11, HC Yellow No. 13, 2-Hydroxyethylamino-5-Nitroanisole, Hydroxyethyl-2-Nitro-p-Toluidine, 4-Hydroxypropylamino-3-Nitrophenol, 3-Methylamino-4-Nitrophenoxyethanol, 3-Nitro-4-Aminophenoxyethanol, 3-Nitro-p-Cresol, 2-Nitro-5-Glyceryl Methylaniline, 4-Nitroguaiacol, 3-Nitro-p-Hydroxyethylaminophenol, 2-Nitro-N-Hydroxyethyl-p-Anisidine, Nitrophenol, 4-Nitrophenyl Aminoethylurea, 4-Nitro-o-Phenylenediamine, 4-Nitro-m-Phenylenediamine, 4-Nitro-o-Phenylenediamine, 2-Nitro-p-Phenylenediamine, 6-Nitro-2,5-Pyridinediamine, 6-Nitro-o-Toluidine, Pigment Blue 15, Pigment Blue 15:1, Pigment Violet 23, Pigment Yellow 13, Solvent Black 3, Solvent Black 5, Solvent Blue 35, Solvent Yellow 85, Solvent Yellow 172, Tetrabromophenol Blue, Tetrahydro-6-Nitroquinoxaline, Tetrahydropyranyl Resorcinol.

The direct dye is preferably selected from Basic Orange 31, Basic Red 51, Basic Red 76, Basic Violet 2, Basic Violet 16, Basic Yellow 40, Basic Yellow 57, Basic Yellow 87, Hc blue 15, Hc blue 17, Hc blue 16, Basic blue 124, HC Blue No. 2, HC Blue No. 12, HC Red No. 3, HC Red No. 10, HC Red No. 11, HC Red No. 13, HC Violet No. 2, HC Yellow No. 2, HC Yellow No. 4, 2-Amino-6-Chloro-4-Nitrophenol, 4-Amino-3-Nitrophenol, 4-hydroxypropylamino-3-nitrophenol and 3-nitro-N-(2-hydroxyethyl)-4-aminophenol.

The conditioning agents can be water-soluble cationic polymers such as Polyquaternium 10, Polyquaternium 6, Polyquaternium 7, Polyquaternium 22 and Polyquaternium 53; fatty amides such as stearamidopropyl dimethylamine; esterquats such as distearoylethyl dimonium chloride, distearoylethyl hydroxyethylmonium methosulphate; lanolin derivatives; cholesterol; pantothenic acid; protein derivatives, provitamins; vitamins; plant extracts; sugars and betaine.

The compositions according to the invention can advantageously also contain silicone- or non-silicone-containing film-forming agents, such as quaternium-80, isoamyl laurate, natural oils and mineral oils.

The compositions according to the invention can contain one or more natural or synthetic additives commonly used in the cosmetic industry to formulate solutions, creams, emulsions, gels, aerosols, foams, powders and granulates. Examples of said additives comprise solvents such as water, low-molecular-weight aliphatic mono- or polyalcohols, esters and ethers thereof, for example alkanols, in particular having 1 to 4 carbon atoms, such as ethanol, n-propanol, isopropanol, butanol and isobutanol; bivalent or trivalent alcohols, in particular having 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerin, diethylene glycol, dipropylene glycol, polyalkylene glycols, such as triethylene glycol, polyethylene glycol, tripropylene glycol and polypropylene glycol; low-molecular-weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular having 3 to 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropylether; esters such as ethyl formate, methyl formate, methyl acetate, ethyl acetate, propyl acetate, butyl acetate, phenyl acetate, ethylene glycol monoethyl ether acetate or acetic acid hydroxyethyl ester; amides such as N-methylpyrrolidone; urea, tetramethyl urea and thiodiglycol.

The following can also be present:
emulsifiers selected from anionic, cationic, non-ionic, amphoteric and zwitterionic emulsifiers; wetting agents; surfactants, such as fatty alcohol sulphates, alkylsulphonates, alkylbenzene sulphonates, alklymethyl ammonium salts, alkylbetaine, α-olefin sulphonates, ethoxylated fatty alcohols, ethoxylated nonylphenols, fatty acid alkanolamines, ethoxylated esters of fatty acids, polyglycol ether sulphates of fatty acids and alkylpolyglycosides,
thickeners, such as higher fatty alcohols, starches, cellulose derivatives, vaseline, paraffin oil, fatty acids and other fatty components in emulsified form, water-soluble polymer thickeners, such as natural gums, guar gum, xanthan gum, carob flour, pectin, dextran, agar-agar, amylose, amylopectin, dextrin, synthetic clays or hydrocolloids, such as polyvinyl alcohol;
auxiliary agents such as electrolytes, antioxidants, sequestering and preserving agents.

The compositions according to the invention can advantageously comprise non-ionic and/or anionic surfactants, such as esters of ethoxylated fatty acids, ethoxylated nonylphenols, ethoxylated fatty alcohols, alkylbenzene sulphonates, olefin sulphonates, alkanolamides of fatty acids, Coco Glucoside, Decyl Glucoside, Lauryl Glucoside, Capryloyl/Caproyl Methyl Glucamide, Lauroyl/Myristoyl Methyl Glucamide, Lauroyl/Myristoyl Methyl Glucamide, Cocoyl Methyl Glucamide, sodium methyl cocoyl taurate, sodium lauroyl methyl isethionate, sodium cocoyl glutamate, sodium cocoyl alaninate, sodium lauroyl glutamate, sodium lauroyl sarcosinate or sodium stearoyl lactylate in a total amount preferably ranging from about 0.1 to 30% by weight, and more preferably from 0.2 to 15% by weight.

Examples of cationic surfactants are quaternary ammonium compounds; ammonium halides such as alkyltrimethylammonium chlorides, dialkyldimethylammonium chlorides and trialkylmethylammonium chlorides. Specific examples are cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, behentrimonium chloride and behentrimonium methosulphate. Other useful cationic surfactants are quaternised protein hydrolysates and stearamidopropyl dimethylamine.

The composition can also contain emulsifiers such as cetearyl olivate, sorbitan olivate or a mixture thereof (Olivem 1000 from Hallstar); polyglyceryl-2 stearate, polyglyceryl-2-oleate, glyceryl stearate or mixtures thereof (Polyaquol 2W and Polyaquol OS2).

In addition to vegetable oils, the composition according to the invention can also contain other conditioning agents, preferably of plant origin or easily biodegradable, such as polyquaternium-10 (cationised cellulose), isoamyl laurate and distearoylethyl-hydroxyethylmonium methosulphate.

EXAMPLES

The ingredients listed in the examples are named according to the INCI nomenclature (European Community Decision 2006/257/EC as amended—International Nomenclature of Cosmetic Ingredients).

Table 1 contains examples of a conditioning mask according to the invention (F2*, F3* and F4*) containing various percentages of azeloglycine (potassium azeloyl diglycinate), a comparative composition without azeloglycine ("placebo" F1), and a composition containing malic acid instead of azeloglycine (F5). Malic acid was selected for comparative purposes because it is one of the molecules most commonly used in the products on the market to perform the function of protecting/repairing the bonds in the hair fibre.

Table 2 contains an example F6* of a coloured conditioner (semipermanent dye) according to the invention and comparator F7.

Table 3 contains an example F8* of an oxidative dye according to the invention.

Table 4 contains the formula F9 of the bleaching powder used in the following examples.

TABLE 1

| | conditioning masks | | | | |
|---|---|---|---|---|---|
| INCI | F1 (%) | F2* (%) | F3* (%) | F4* (%) | F5 (%) |
| AQUA (WATER) | Q.s. to 100 | Q.s. to 100 | Q.s. to 100 | Q.s. to 100 | Q.s. to 100 |
| CETEARYL ALCOHOL | 5.0 | 5.0 | 5.0 | 5.0 | 5.0 |
| ETHYLHEXYL STEARATE | 3.0 | 3.0 | 3.0 | 3.0 | 3.0 |
| BEHENTRIMONIUM CHLORIDE | 3.0 | 3.0 | 3.0 | 3.0 | 3.0 |
| DIMETHICONE | 3.0 | 3.0 | 3.0 | 3.0 | 3.0 |
| CAPRYLIC/CAPRIC TRIGLYCERIDE | 2.0 | 2.0 | 2.0 | 2.0 | 2.0 |
| GLYCERIN | 2.0 | 2.0 | 2.0 | 2.0 | 2.0 |
| MYRISTYL ALCOHOL | 2.0 | 2.0 | 2.0 | 2.0 | 2.0 |
| POTASSIUM AZELOYL DIGLYCINATE | — | 1.0 | 2.0 | 3.0 | — |
| MALIC ACID | — | — | — | — | 5.0 |
| PROPYLENE GLYCOL | 1.0 | 1.0 | 1.0 | 1.0 | 1.0 |
| DICETYLDIMONIUM CHLORIDE | 1.0 | 1.0 | 1.0 | 1.0 | 1.0 |
| PRUNUS AMYGDALUS DULCIS OIL | 1.0 | 1.0 | 1.0 | 1.0 | 1.0 |
| QUATERNIUM-80 | 1.0 | 1.0 | 1.0 | 1.0 | 1.0 |
| LACTIC ACID | 1.0 | 1.0 | 1.0 | 1.0 | 1.0 |
| PARFUM (FRAGRANCE) | 1.0 | 1.0 | 1.0 | 1.0 | 1.0 |
| ISOPROPYL ALCOHOL | 1.0 | 1.0 | 1.0 | 1.0 | 1.0 |
| HYDROXYPROPYL GUAR HYDROXYPROPYLTRIMONIUM CHLORIDE | 0.5 | 0.5 | 0.5 | 0.5 | 0.5 |
| DIMETHICONOL | 0.50 | 0.50 | 0.50 | 0.50 | 0.50 |
| LACTIC ACID | to pH 4 | to pH 4 | to pH 4 | to pH 4 | to pH 4 |

TABLE 2

| | coloured conditioner (semipermanent dye) | |
|---|---|---|
| INCI | F6* (%) | F7 (%) |
| AQUA (WATER) | Q.s. to 100 | Q.s. to 100 |
| PROPYLENE GLYCOL | 6 | 6 |
| CETEARYL ALCOHOL | 5 | 5 |
| GLYCERIN | 5 | 5 |
| DISTEAROYLETHYL HYDROXYETHYLMONIUM METHOSULPHATE | 1.5 | 1.5 |
| BASIC RED 51 | 1 | 1 |
| CETYL ALCOHOL | 1 | 1 |
| STEARAMIDOPROPYL DIMETHYLAMINE | 1 | 1 |
| POTASSIUM AZELOYL DIGLYCINATE | 1 | — |
| PRESERVATIVE | 1 | 1 |
| LACTIC ACID | 0.5 | 0.5 |
| PARFUM (FRAGRANCE) | 0.5 | 0.5 |

TABLE 3

| | oxidative dye |
|---|---|
| INCI | F8* (%) |
| AQUA (WATER) | Q.s. to 100 |
| CETEARYL ALCOHOL | 8 |
| CETEARETH-50 | 7 |
| STEARYL ALCOHOL | 6 |
| PROPYLENE GLYCOL | 5 |
| LAURYL ALCOHOL | 3 |
| PEG-40 HYDROGENATED CASTOR OIL | 2 |
| AMMONIA | 1.8 |
| TOLUENE-2,5-DIAMINE SULPHATE | 1.48 |
| COCAMIDOPROPYL BETAINE | 1.2 |
| MYRISTYL ALCOHOL | 1.2 |

TABLE 3-continued oxidative dye

| INCI | F8* (%) |
|---|---|
| ETHANOLAMINE | 1.1 |
| POTASSIUM AZELOYL DIGLYCINATE | 2.5 |
| PARFUM (FRAGRANCE) | 0.8 |
| DECYLTETRADECANOL | 0.7 |
| SODIUM SULPHITE | 0.4 |
| RESORCINOL | 0.39 |
| ERYTHORBIC ACID | 0.3 |
| 2-METHYLRESORCINOL | 0.28 |
| POLYQUATERNIUM-22 | 0.25 |
| EDTA | 0.2 |
| BISABOLOL | 0.1 |
| M-AMINOPHENOL | 0.083 |
| 2,4-DIAMINOPHENOXYETHANOL HCL | 0.036 |

TABLE 4 bleaching powder

| INCI | F9 (%) |
|---|---|
| POTASSIUM PERSULPHATE | 50.0 |
| SODIUM SILICATE | 20.0 |
| MAGNESIUM CARBONATE | 8.0 |
| SODIUM STEARATE | 5.0 |
| AMMONIUM PERSULPHATE | 5.0 |
| SODIUM METASILICATE | 4.0 |
| EDTA | 2.0 |
| HYDROXYETHYLCELLULOSE | 2.0 |
| PARAFFINUM LIQUIDUM (MINERAL OIL) | 2.0 |
| XANTHAN GUM | 1.0 |
| POTASSIUM ALGINATE | 0.5 |
| SILICA | 0.5 |
| HYDROXYPROPYL GUAR | 0.5 |
| HYDROXYPROPYLTRIMONIUM CHLORIDE | |
| PARFUM (FRAGRANCE) | 0.3 |

Example 1: Lightening

The skilled person is aware that it is easier to lighten natural hair than hair which has already undergone cosmetic dyeing. Cosmetically coloured locks were therefore used for the lightening evaluation. Said type of lock is the best suited to comparing different bleaching products. The test is conducted on level 10 Very Light Blonde IHIP (International Hair Importers and Products) locks. 3 locks are used per test group. An Alfaparf EOC CUBE 3 (natural dark chestnut) oxidative dye is applied, mixed at the ratio of 1:1.5 with Alfaparf Milano Oxid'o 10 volumes. The product is left to act for 35 minutes at 30° C., then rinsed, and the locks are dried with a hairdryer. The starting colour level is then measured (see below). Bleaching powder F9 is then applied mixed with activator Alfaparf Milano Oxid'o 30 vol at the ratio of 1:2, and left to act for 40 minutes at 30° C. The locks are then rinsed, washed with conventional shampoo and dried.

The same treatment is performed on another set of three locks after mixing the Wella Wellaplex no. 1 Bond Maker product with the bleaching powder and activator mixture, according to the specific instructions for use. Finally, the hair level after bleaching is measured.

A Konica Minolta CM-2500d colorimeter is used to analyze the locks. The instrument expresses the colour level as CIE coordinates L, a, b, C, h (D 65), wherein:
L(D65) indicates brightness, and corresponds to height of tone a(D65) is the red/green coordinate b(D65) is the yellow/blue coordinate C*(D65) represents Chroma and corresponds to the yellow/orange residue.

D65 corresponds to illuminant CIE D65, which is the internationally recognised emission standard for outdoor daylight, as defined in standard ISO 10977:1993.

6 measurements per lock are taken on the hair length, starting at the root and moving down to the tips. The instrument averages the various measurements, generating the colorimetric coordinates of the lock. The data are processed with SpectraMagic NX (Konica Minolta) software.

The colorimetric coordinate values L*(D65), a*(D65) and b*(D65) are entered in Excel spreadsheets to generate the bleaching parameters. The lightening level can be calculated from the value of L (D65), using a specific pre-prepared calibration curve. To calculate by how many levels a cosmetic composition has lightened the hair, the starting level is subtracted from the level measured after bleaching. The results are set out in Table 5.

TABLE 5 lightening performance

| Treatment | MEAN LIGHTENING LEVEL | SD |
|---|---|---|
| Formula F9 | 6.77 | 0.04 |
| Formula F9 + Wellaplex no1 Bond Maker | 6.11 | 0.21 |

If Wella Wellaplex no. 1 Bond Maker is added to the bleaching powder there is a marked loss of lightening performance, probably due to a diluting effect of the bleaching mixture.

Example 2: Differential Scanning Calorimetry (DSC)

Differential scanning calorimetry can be used to measure the enthalpy of keratin denaturation (delta HD), which is controlled by the integrity of the alpha-helix structure, and the keratin denaturation temperature (TD), which depends on the density of the bonds in the cortex (Wortmann et al., J Cosmet. Sci. July-August 2002; 53(4):219-28; Wortmann et al., J Cosmet. Sci. July-August 2007; 58(4):311-7).

Aggressive cosmetic treatments cleave the chemical bonds in the hair, leading to a reduction in TD. A repair treatment should restore the peak temperature to the level of natural virgin (untreated) hair, demonstrating its ability to restore the bond density in the cortex.

A METTLER TOLEDO STARE SYSTEM DSC 3 differential scanning calorimeter was used for this study. The evaluation was conducted on IHIP level 2 locks of virgin human hair. One lock was left virgin, ie. untreated (a). Other 8 locks were subjected to a bleaching treatment using formula F9. The bleaching powder was mixed with the activator Alfaparf Milano Oxid'o 30 vol at the ratio of 1:2, applied to the locks and left to act for 40 minutes at 30° C. The locks were then rinsed, washed with conventional shampoo and blotted on paper.

As the preliminary data and those reported in the literature demonstrate that a bleaching treatment gives rise to a marked reduction in TD, it is possible to evaluate how "bond rebuilder" compositions can restore the bond density.

One lock was thus left bleached and not subjected to other treatments. One virgin lock was subjected to the same bleaching treatment but adding Wella Wellaplex no. 1 Bond Maker to the mixture of bleaching powder and activator, according to the instructions for use. After bleaching, the lock was rinsed and blotted dry; the product Wellaplex no. 2 Bond Stabilizer, processed according to the instructions for use, was then applied.

Four bleached locks were treated with formulations F1, F2*, F3* and F4*, left for the product to act for 10 minutes, and then rinsed and dried. Two bleached locks were treated with formulas F6* and F7, left for the product to act for 15 minutes, and then rinsed and dried. A last bleached lock was treated with a semipermanent dye containing a "bonding" ingredient present on the market, according to the instructions for use.

Portions about 2 mm long were cut from the tips of the 10 locks. About 6.0±0.5 mg of said pieces of fibre were weighed in a stainless steel crucible together with 40 microlitres of water. The container was closed and left to stand for 24 hours to achieve a hydration balance in the fibres. The crucible was then inserted into the furnace of the instrument, and the analysis protocol was started, involving a heating ramp from 30 to 180° C., with a heating rate of 10° C./min. The measurement was repeated three times per lock. The data collected were processed with STARe software (Mettler Toledo). Table 6 shows the results obtained. The mean value of TD measured from the three crucibles (MEAN TD), the standard deviation (SD), the delta of TD compared with bleached hair (delta TD), and the percentage difference relative to delta TD between virgin and bleached hair (10.09° C., difference %), are shown. The chart in FIG. 1 shows the mean denaturation temperatures TD measured from the various samples.

TABLE 6

DSC analysis of masks

| TREATMENT | MEAN TD | SD | DELTA TD | % DIFFERENCE |
| --- | --- | --- | --- | --- |
| NATURAL LEVEL 2 (a) | 154.2 | 0.19 | 10.09 | |
| BLEACHED (b) | 144.1 | 0.16 | 0 | |
| F1 placebo mask | 146.4 | 0.09 | 2.3 | 23% |
| F2* mask with 1% azeloglycine | 151.6 | 0.22 | 7.5 | 75% |
| F3* mask with 2% azeloglycine | 154.8 | 0.17 | 10.7 | 106% |
| F4* mask with 3% azeloglycine | 155.2 | 0.06 | 11.1 | 110% |
| Wellaplex complete treatment (c) | 154.5 | 0.31 | 10.40 | 104% |
| F6* semipermanent dye with 1% azeloglycine | 151.60 | 0.18 | 7.5 | 74.3% |
| F7 semipermanent dye without azeloglycine | 147.1 | 0.02 | 3 | 29.7% |
| Market benchmark semipermanent dye containing bonding ingredient | 148.7 | 0.62 | 4.6 | 45.6% |

The data analysis demonstrates that a bleaching treatment gives rise to a significant reduction in TD compared to virgin hair (−10.09° C.). Application of "placebo" formulation F1, not containing azeloglycine, gives rise to a modest recovery of TD (+23%). Formulations F2* to F4* give rise to a more marked recovery of TD, with a dose-dependent effect (+75% for F2*; +106% for F3*; +110% for F4*). The Wellaplex treatment also gives rise to total recovery of TD (+104%). It is therefore demonstrated that treatments containing azeloglycine can restore TD, and therefore the bond density in the hair cortex, in a single step and with a single application, in the same way as the two-component treatments present on the market. The data further demonstrate that in a semipermanent dye formulation, azeloglycine restores the bond density in the hair fibre better than similar market-leading products.

A similar test was conducted by applying the permanent dye according to the invention F8 to locks bleached as described above, by comparison with a market benchmark product containing "bonding" ingredients. Both hair dyes were mixed with Alfaparf Milano Oxid'o 20 vol at the ratio of 1:1.5, applied to the locks and left to act for 35 minutes at 30° C. The locks were then rinsed, washed with shampoo base and dried. The data collected were processed with STARe software (Mettler Toledo). Table 7 shows the results obtained.

TABLE 7

DSC analysis for oxidative dyeing

| TREATMENT | MEAN TD | SD | DELTA TD | % DIFFERENCE |
| --- | --- | --- | --- | --- |
| NATURAL LEVEL 2 (a) | 154.2 | 0.19 | 10.09 | |
| BLEACHED (b) | 144.1 | 0.16 | 0 | |
| F8* oxidative dye with 2.5% azeloglycine | 148.83 | 0.75 | 4.73 | 46.9% |
| Market benchmark oxidative dye with bonding claim | 149.3 | 0.43 | 5.2 | 51.5% |

Figure 2:
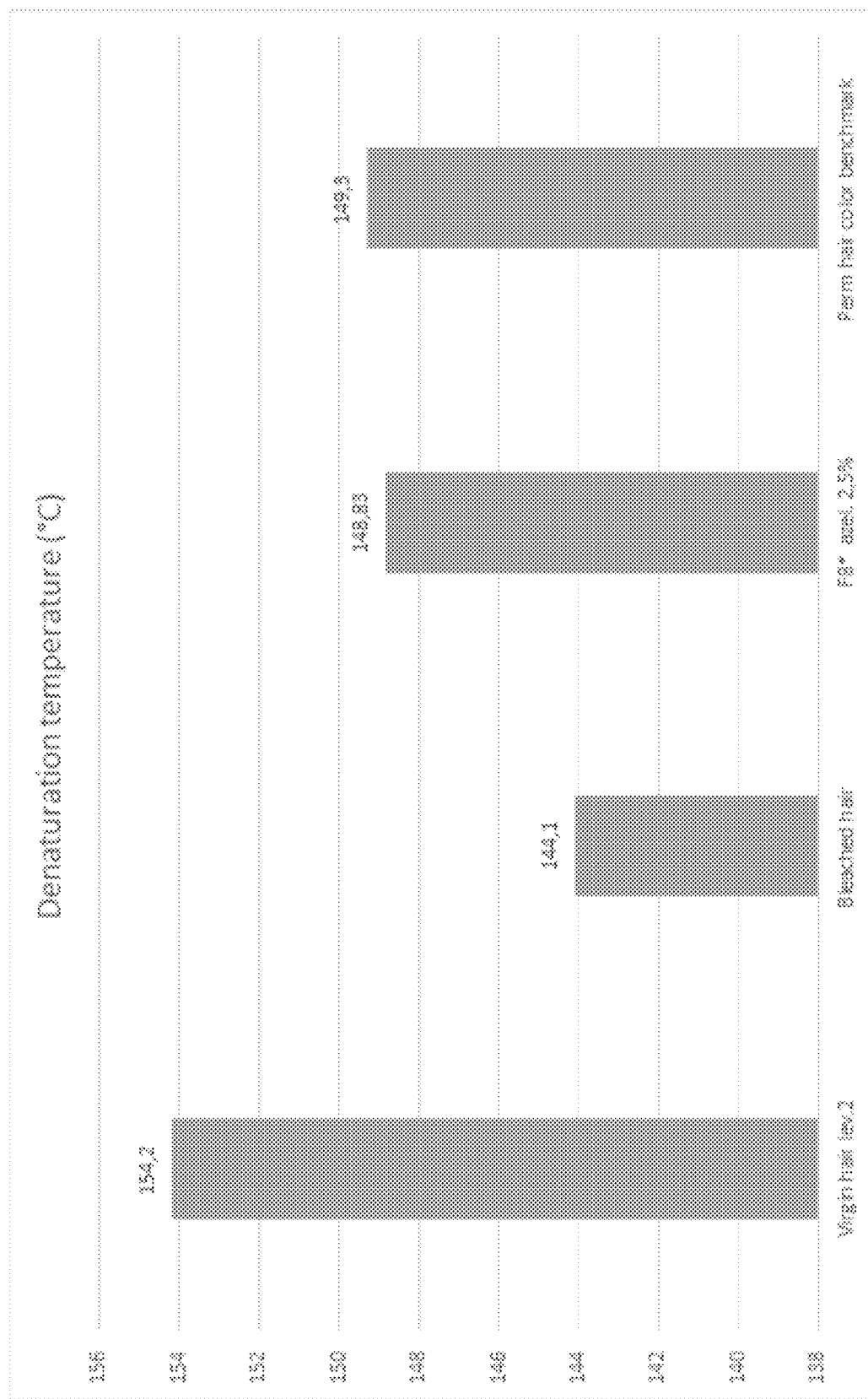
FIG. 2 shows the mean denaturation temperatures TD measured from the various samples.

The chart in FIG. 2 shows the mean denaturation temperatures TD measured from the various samples.

Taking account of the standard deviations, the test demonstrates that the oxidative dye with azeloglycine F8* (according to the invention) is comparable with the market benchmark in terms of restoring the bond density of the hair.

Example 3: Combability on Dry and Wet Hair

The combability test involves the use of a DIA-STRON MTT175 dynamometer to measure the work required to comb locks of hair. The friction when the comb (connected to the instrument) passes through the lock is measured. The combability data are recorded by the software of the instrument, analysed, and expressed in Joules. The test is conducted on 3 locks per treatment.

The evaluation was conducted on IHIP level 2 locks of human virgin hair bleached with formula F9. The bleaching powder was mixed with the activator Alfaparf Milano Oxid'o 30 vol at the ratio of 1:2, applied to the locks and left to act for 40 minutes at 30° C. The locks were then rinsed, washed with shampoo base and blotted on paper. The locks were then treated with formulation F3* (according to the invention) or F5 (containing malic acid), left for the product to act for 10 minutes, and then rinsed, dried in a dryer at 55° C. for 30 minutes, and measured with the dynamometer.

The test results on dry and wet hair are shown in Tables 8 and 9 respectively. The percentage indicates the average difference in the work required to comb the hair due to greater friction of the comb on the hair fibres. A positive difference therefore indicates lesser combability, while a negative difference indicates greater combability. The measurements on wet hair are taken by immersing the locks in tapwater at room temperature and removing the excess water before performing the measurement.

TABLE 8

Dry hair combability test with dynamometer

| Formulation applied to bleached hair | TOTAL WORK (JOULES) | SD | % WORK DIFFERENCE |
|---|---|---|---|
| F3* | 0.70E−04 | 3.65E−05 | — |
| F5 | 1.03E−04 | 4.56E−05 | +46% |

TABLE 9

Wet hair combability test with dynamometer

| Formulation applied to bleached hair | TOTAL WORK (JOULES) | SD | % WORK DIFFERENCE |
|---|---|---|---|
| F3* | 0.95E−03 | 2.55E−04 | — |
| F5 | 1.16E−03 | 3.68E−04 | +22% |

The data demonstrate that the composition according to the invention (F3*) has a better cosmetic effect, leaving the hair more manageable and combable than formula F5, which is identical in terms of formulation but contains malic acid instead of azeloglycine.

It was therefore decided to compare formulation F3* (according to the invention) with the Wellaplex treatment. Three locks, bleached according to the protocol specified above, were treated with formulation F3*, left for the product to act for 10 minutes, rinsed, dried in a dryer at 55° C. for 30 minutes, and measured with the dynamometer. Three other IHIP level 2 locks of human virgin hair were subjected to the same bleaching treatment, with the addition of Wella Wellaplex no. 1 Bond Maker to the mixture of bleaching powder and activator, according to the instructions for use. After bleaching, the locks were rinsed and blotted dry; the Wellaplex no. 2 Bond Stabilizer product, processed according to the instructions for use, was then applied. The test results on dry and wet hair are shown in Tables 10 and 11 respectively.

TABLE 10

Dry hair combability test with dynamometer

| Formulation applied to bleached hair | TOTAL WORK (JOULES) | SD | % WORK DIFFERENCE |
|---|---|---|---|
| F3* | 0.90E−04 | 0.61E−04 | — |
| Wellaplex complete treatment | 1.88E−04 | 1.16E−04 | 110% |

TABLE 11

Wet hair combability test with dynamometer

| Formulation applied to bleached hair | TOTAL WORK (JOULES) | SD | % DIFFERENCE |
|---|---|---|---|
| F3* | 1.07E−03 | 2.52E−04 | — |
| Wellaplex complete treatment | 1.85E−03 | 5.00E−04 | 73% |

The data demonstrate that the composition according to the invention (F3*) has a better cosmetic effect, leaving the hair more manageable and combable, than the complete Wellaplex treatment.

Example 4: Tensile Strength Test

The test involves subjecting the lock to repeated combing to evaluate the efficacy of various cosmetic treatments against damage caused to the hair by mechanical stress, such as brushing. The more the hair is weakened by prior chemical treatments such as bleaching, dyeing and permanent styling, the lower its resistance to mechanical stress will be.

The locks are attached to a specific support and subjected to repeated combing for one hour by a multi-comb rotary system that moves at the speed of 85 rpm, giving a total of about 20,400 combing strokes/hour. The rotary system is equipped with 4 identical antistatic combs. The locks are weighed before and after the test, and the weight difference is calculated. The greater the weight loss, the greater the breakage of hair fibres. The results of this test are directly correlated with the degree of hair damage; the more badly damaged the hair, the greater the weight loss. "Restructuring" cosmetic treatments give rise to a reduction in the number of hair fibre breakages, with a consequent reduction in weight loss.

The evaluation was conducted on IHIP level 2 locks of human virgin hair bleached with formula F9. The bleaching powder was mixed with the activator Alfaparf Milano Oxid'o 30 vol at the ratio of 1:2, applied to the locks and left to act for 40 minutes at 30° C. The locks were then rinsed, washed with shampoo base and blotted on paper. The locks were then treated with formulation F3* (according to the invention) or F5 (containing malic acid), left for the product to act for 10 minutes, and rinsed and dried with a hairdryer. The test is conducted in an air-conditioned room with a temperature of 22-25° C. and 50-60% relative humidity. The results are shown in Table 12.

TABLE 12

Tensile strength test

| Formulation applied to bleached hair | STARTING WEIGHT (grams) | FINAL WEIGHT (grams) | WEIGHT LOSS (grams) | SD | % DIFFERENCE |
|---|---|---|---|---|---|
| F3* | 1.85047 | 1.70648 | −0.14399 | 0.05695 | — |
| F5 | 1.90394 | 1.61099 | −0.29295 | 0.05307 | +103% |

The data demonstrate that the composition according to the invention (F3*) gives hair damaged by a bleaching treatment better resistance to repeated combing than formula F5 containing malic acid, thus suggesting that azeloglycine has a better restructuring effect than malic acid.

It was therefore decided to compare formulation F3* (according to the invention) with the Wellaplex treatment. Three IHIP level 2 locks of human virgin hair 1, bleached according to the protocol specified above, were treated with formulation F3*, left for the product to act for 10 minutes, rinsed, dried in a dryer at 55° C. for 30 minutes, and measured with the dynamometer. Three other IHIP level 2 locks of human virgin hair 1 were subjected to the same bleaching treatment, with the addition of Wella Wellaplex no. 1 Bond Maker to the mixture of bleaching powder and activator, according to the instructions for use. After bleaching, the locks were rinsed and blotted dry; the Wellaplex no. 2 Bond Stabilizer product, processed according to the instructions for use, was then applied. The results are shown in Table 13.

TABLE 13

| Tensile strength test | | | | | |
|---|---|---|---|---|---|
| Formulation applied to bleached hair | STARTING WEIGHT (grams) | FINAL WEIGHT (grams) | WEIGHT LOSS (grams) | SD | % DIFFERENCE |
| F3* | 1.84166 | 1.49917 | −0.34249 | 0.05806 | — |
| Wellaplex complete treatment | 1.84935 | 1.41637 | −0.43298 | 0.02795 | 26% |

Once again, the data demonstrate that the composition according to the invention (F3*) gives hair damaged by a bleaching treatment better resistance to repeated combing than the complete Wellaplex treatment, thus suggesting that said inventive formula has a better restructuring effect.

Example 5: Shine Test

The SAMBA Hair System instrument made by Bossa Nova Technologies was used to conduct this test. The instrument is equipped with a system of light sources with light polarisation filters, a sensor, a cylinder to house the samples, and software to process the data collected. The system uses various formulas to characterize the specular and diffused profiles: Reich-Robbins, TRI, Stamm, Guiolet and Bossa Nova Technologies.

The evaluation was conducted on IHIP level 2 locks of virgin human hair. A set of 3 locks was bleached with formula F9.

The bleaching powder was mixed with the activator Alfaparf Milano Oxid'o 30 vol at the ratio of 1:2, applied to the locks and left to act for 40 minutes at 30° C.

The locks were then rinsed, washed with shampoo base and blotted on paper. The locks were then treated with formulation F3* (according to the invention), left for the product to act for 10 minutes, and rinsed and dried with a hairdryer.

Another set of 3 IHIP level 2 locks of virgin human hair were subjected to the same bleaching treatment, with the addition of Wella Wellaplex no. 1 Bond Maker to the mixture of bleaching powder and activator, according to the instructions for use.

After bleaching, the lock was rinsed and blotted dry; the product Wellaplex no. 2 Bond Stabilizer, processed according to the instructions for use, was then applied.

Table 14 shows the mean values of the two sets of locks, expressed as percentage difference. The proprietary formula (Bossa Nova Technologies) was used as calculation formula. Positive values indicate a better shine, and a better shine is an indicator of less damaged hair.

TABLE 14

| Shine test | | | |
|---|---|---|---|
| Formulation applied to bleached hair | BOSSA NOVA COEFFICIENT | SD | % DIFFERENCE |
| F3* | 4.91 | 0.41 | — |
| Wellaplex complete treatment | 4.39 | 0.21 | −10% |

The data demonstrate that the composition according to the invention (F3*) gives hair damaged by a bleaching treatment a better shine than the complete Wellaplex treatment.

The invention claimed is:

1. A method for the restructuring treatment of keratinic fiber, said method consisting of applying on said keratinic fiber of a composition comprising potassium azeloyl diglycinate in weight percentages ranging between 0.1 and 6% for 25 to 40 minutes; and
rinsing.

2. The method according to claim 1, wherein said keratinic fiber are human hair.

3. The method according to claim 1, wherein said potassium azeloyl diglycinate is in weight percentages ranging between 0.5 and 3%.

4. The method according to claim 1 in which the composition further comprises direct dyes and has a pH ranging between 3 and 9.

5. The method according to claim 4, wherein said direct dyes has a pH ranging between 3 and 6.

6. The method according to claim 1 in which the composition further comprises oxidative dyes and has a pH ranging between 8 and 11.

7. The method according to claim 1 in which the composition is in the form of an O/W (oil-in-water) or W/O (water-in-oil) emulsion, liquid, two-phase liquid, gel, transparent gel, oil, aerosol or mousse.

8. The method according to claim 1 in which the composition comprises
solvents, wetting agents, thickeners, conditioning agents, auxiliary agents, nonionic and/or anionic surfactants and
emulsifier selected from anionic, cationic, non-ionic, amphoteric or zwitterionic emulsifiers.

\* \* \* \* \*